(12) United States Patent
Rashidi et al.

(10) Patent No.: US 9,402,750 B2
(45) Date of Patent: Aug. 2, 2016

(54) TESTING APPARATUS FOR AN ORTHOPAEDIC SPECIMEN SUCH AS A KNEE IMPLANT PROSTHESIS

(71) Applicants: Majid Rashidi, Pepper Pike, OH (US); Alon Katz, Akron, OH (US); Paul D. Postak, University Heights, OH (US); A. Seth Greenwald, Cleveland Heights, OH (US)

(72) Inventors: Majid Rashidi, Pepper Pike, OH (US); Alon Katz, Akron, OH (US); Paul D. Postak, University Heights, OH (US); A. Seth Greenwald, Cleveland Heights, OH (US)

(73) Assignee: ORTHOPAEDIC RESEARCH LABORATORIES, Cleveland, OH (US)

( * ) Notice: Subject to any disclaimer, the term of this patent is extended or adjusted under 35 U.S.C. 154(b) by 235 days.

(21) Appl. No.: 13/841,645

(22) Filed: Mar. 15, 2013

(65) Prior Publication Data

US 2014/0260579 A1 Sep. 18, 2014

(51) Int. Cl.
*G01L 1/00* (2006.01)
*A61F 2/76* (2006.01)
*A61F 2/46* (2006.01)
*A61F 2/38* (2006.01)

(52) U.S. Cl.
CPC . *A61F 2/76* (2013.01); *A61F 2/468* (2013.01); *A61F 2/38* (2013.01)

(58) Field of Classification Search
CPC ................................. A61F 2/76; A61F 2/38
See application file for complete search history.

(56) References Cited

U.S. PATENT DOCUMENTS 7,493,828 B2   2/2009  Greenwald et al.
7,823,460 B2   11/2010 White

*Primary Examiner* — Lisa Caputo
*Assistant Examiner* — Brandi N Hopkins
(74) *Attorney, Agent, or Firm* — Fay Sharpe LLP

(57) ABSTRACT

A testing apparatus is provided for exposing an associated specimen to movement along multiple axes. A test chamber is dimensioned to receive the associated specimen. A first device is operatively connected to the test chamber to impose a first, rotational movement on the associated specimen, a second device is operatively connected to the test chamber to impose a second, rotational movement different than the first movement on the associated specimen, a third device is operatively connected to the test chamber to impose a generally planar movement or linear translation on the associated specimen, and a fourth device is operatively connected to the test chamber to impose a load force on the associated specimen. A drive mechanism is operatively connected to the first, second, third, and fourth devices so that the movements and forces imposed by respective ones of the devices are commonly driven by the drive mechanism.

20 Claims, 13 Drawing Sheets

TESTING APPARATUS FOR AN ORTHOPAEDIC SPECIMEN SUCH AS A KNEE IMPLANT PROSTHESIS

BACKGROUND OF THE DISCLOSURE

This disclosure relates to a testing apparatus for orthopaedic specimens. In particular, this disclosure relates to a testing apparatus that is used to apply motions and forces to a test specimen(s) in a manner representative of what a prosthesis may encounter when implanted.

Various suppliers design and manufacture orthopaedic specimens in an effort to evaluate the suitability of a particular design for use such as a prosthesis, for example, a knee implant. Before these new designs are available for use, specimens must undergo rigorous testing under prescribed conditions. For example, ISO 14243 is a standard that sets forth criteria for evaluating the design and materials of knee implants, and particularly aids in evaluating the wear of test specimens. Imposed forces result in defined, discrete motions and the motions are coordinated with one another in a preselected environment (e.g., a force(s) applied in a particular pattern, for a desired time, at a desired velocity, and in a particular environment). The test is typically conducted for millions of cycles, for example, 5,000,000 to 10,000,000 cycles at 1 Hz. The test is extensive, carefully controlled, and test conditions are closely monitored, and preferably the testing apparatus can simultaneously test multiple, individual specimens under similar conditions.

For example, with reference to a knee implant and the noted ISO standard, a first defined motion ($\Theta_y$) caused by the moment ($M_y$) is generally referred to as flexion/extension and relates to rotation about one axis of an orthogonal coordinate system. The driving force or torque, to achieve this motion is applied to the specimen, and particularly the femoral component of the test specimen, while the other component is representative of the tibia.

A second defined motion ($\Theta_z$) caused by the moment ($M_z$) is rotation about one of the axes of the orthogonal coordinate system. This movement is representative of the movement of the tibia.

A third motion (X) caused by the force ($F_x$) is referred to as linear translation along one of the axes of the orthogonal coordinate system. In other words, this relates to forces that result in forward and backward motion imposed on the test specimen.

The fourth action relates to an axial compressive force ($F_z$) imposed on the test specimen. This axial force can rapidly increase in a short period of time. For example, a dynamic compressive load can rapidly increase by 1800 N in 0.03 seconds. Further, the dynamic, load must be able to exceed a force of 2600 N.

These motions and forces must be synchronized. At least three of the forces/motions/actions are periodic. Further, the testing system must maintain this synchronized action on multiple specimens over an extended period of time (e.g. testing of multiple specimens through millions of cycles takes a few months to complete).

Conventional, commercially available systems use multiple electrohydraulic actuators to achieve the various motions and load magnitudes required under the ISO standard. Unfortunately, these electrohydraulic actuators are relatively expensive. Further, the electrohydraulic actuators are not particularly effective in measuring smaller forces (e.g. on the order of less than 70 N) nor do the electrohydraulic actuators have good resolution. Also, use of the electrohydraulic actuators and associated controls require expensive sensors in an effort to achieve synchronization or phased movement as required under the ISO standard. As a result, the use of multiple electrohydraulic actuators, and the associated sensors and controls therefor, results in a test apparatus that is unduly expensive. These problems are magnified when the test apparatus is designed to simultaneously test multiple test specimens.

Accordingly, a need exists for an alternate test apparatus that is dependable, durable, accurate, easy-to-use, economical to manufacture and use, and can be easily adapted to multiple stations to permit simultaneous testing of multiple specimens.

SUMMARY OF THE DISCLOSURE

An improved testing apparatus exposes an associated specimen to forces and motions along and about multiple axes. The testing apparatus includes a test chamber dimensioned to receive the associated specimen. A drive mechanism is connected to the first, second, third, and fourth devices so that the forces/motions imposed on the associated test specimen are commonly driven.

In one preferred arrangement, a first device imposes a first, rotational movement on the associated specimen. A second device imposes a second, rotational movement different than the first rotational movement, on the associated specimen. A third device imposes a generally linear translation on the associated specimen. A fourth device imposes a dynamic force on the associated specimen.

The first device is preferably configured to rotate the associated specimen about a first axis, while the second device is preferably configured to rotate the associated specimen about a second axis orthogonal to the first axis.

The third device is preferably configured to apply linear translation to the associated specimen, while the fourth device is preferably configured to impose a periodic, dynamic, compressive force on the associated specimen.

The drive mechanism preferably includes first and second cams that are configured to rotate together, and in one preferred embodiment the first and second cams are generally annularly shaped to provide first, second, third, and fourth cam profiles.

Associated first, second, third, and fourth followers each operatively engage one of the first and second cams, and in a preferred arrangement, each of the followers engages one of the profiles.

Each of the first, second, third, and fourth devices includes a restoring member configured to urge the first, second, third, and fourth followers against one of the first and second cams, and preferably urges one of the followers against one of the profiles.

A method of testing the specimen includes placing the specimen in a test chamber, imposing a dynamic, compressive force on the specimen, providing a substantially linear translation on the specimen about one of the axes, applying rotational motions about the other two orthogonal axes, and commonly driving the force, linear translation, and the two rotations with a drive mechanism.

The force imposing step includes applying a dynamic, periodic, compressive force on the specimen.

The commonly driving step includes rotating first and second cams together.

The method further includes providing first, second, third, and fourth followers that engage at least one of the first and second cams.

The driving step preferably includes providing first and second generally annular cams rotated about a single axis where each cam has an inner and outer profile and each profile is engaged by at least one of first, second, third, and fourth followers.

The method further includes urging each of the first, second, third, and fourth followers against a respective profile.

The method may also include assembling multiple testing apparatus together in a coordinated configuration in order to simultaneously test multiple, individual specimens under the same conditions.

The assembly of multiple testing apparatus is preferably commonly driven by the same drive mechanism, preferably the first and second cams.

A primary advantage of the disclosure relates to eliminating use of electrohydraulic actuators (and associated controls and sensors) in the testing apparatus.

Another benefit of the disclosure is the preparation of a testing apparatus that is dependable, durable, and accurate.

Still another advantage relates to the ability to easily replicate multiple testing apparatus into a multiple station system.

Yet another benefit resides in the reduced cost to manufacture a reliable system.

Still other benefits and advantages will become apparent to those skilled in the art upon reading and understanding the following detailed description.

DETAILED DESCRIPTION OF THE PREFERRED EMBODIMENT

Figure 1:
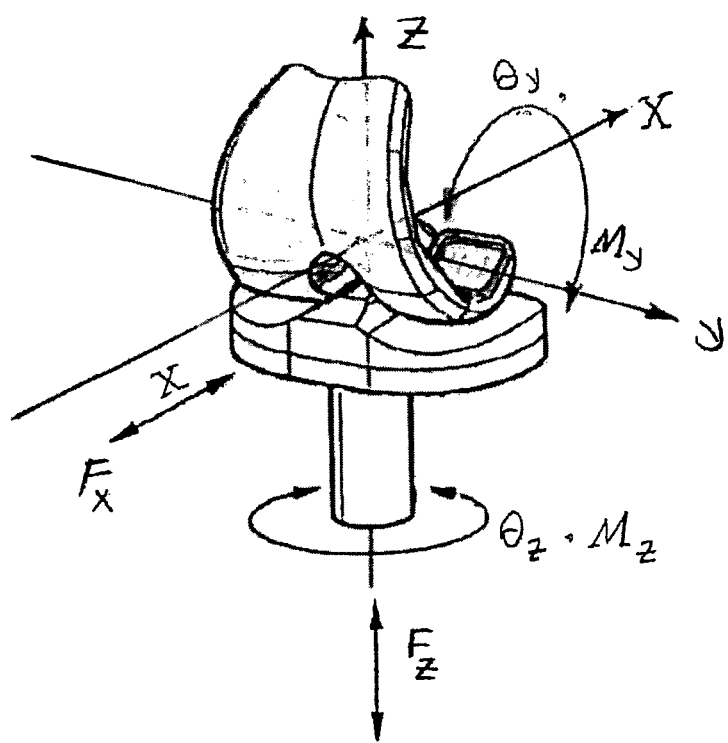
FIG. 1 defines the orthogonal coordinate system and the forces/motions.
Figure 2:
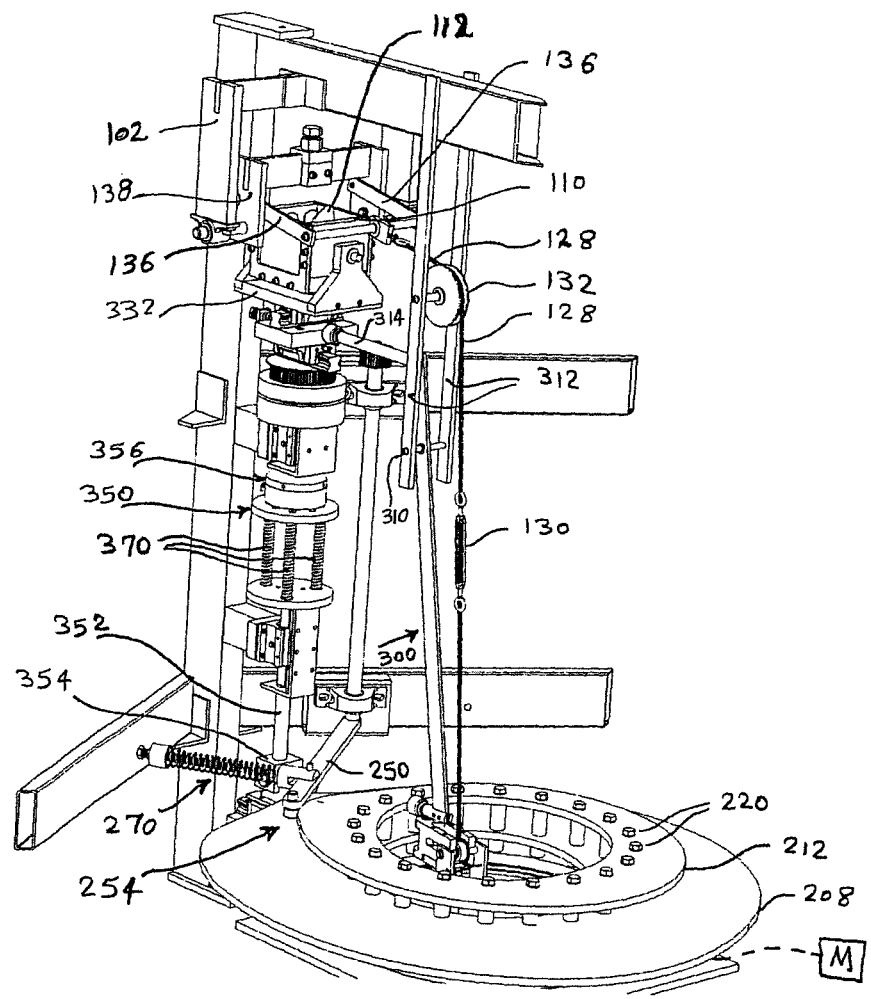
FIG. 2 is a perspective view of a testing apparatus.

The machine described herein produces three kinematic motions and a dynamic force along the three axes of an orthogonal coordinate system which is fixed in space with its origin located within the specimen. FIG. 1 depicts the set of orthogonal system axes with the kinematic motions and dynamic force schematically shown. For example, the first kinematic motion $[\Theta_y]$ is rotation about the first axis of the orthogonal coordinates which is produced by the moment $M_y$. The second kinematic motion $[\Theta_x]$ is rotation about the second axis produced by the moment $M_z$. The dynamic force $F_z$ acts along the same axis. The third kinematic motion is linear translation [X] which takes place along the third axis in response to the force F. FIG. 2 shows a testing apparatus 100 supported by a frame 102 that includes a test chamber 110 for receiving an associated test specimen 112. The test chamber 110 is preferably configured so that the lower portion of test specimen 112 when mounted therein does not move relative to the test chamber. The test chamber 110 has a sealed cavity to receive a fluid at a predetermined temperature and that also meets other parameters specified by the testing protocol. The fluid serves as a medium having some characteristics comparable to those experienced in a human body. For example, if the test specimen is ultimately intended for use as an artificial knee implant, then the specimen will be immersed in the fluid and maintained at a temperature that is representative of the human body.

When mounted in the test chamber, selected forces and motions are imposed on the test chamber and consequently on the associated specimen. With initial reference to FIGS. 2 and 3, the preferred testing apparatus 100 includes a first device 120 that is operatively connected to the test chamber to direct a first force that is configured relative to the test chamber to impose a rotational motion on the test specimen. The first device 120 preferably includes an elongated flexible member such as a cable or wire 122 having a first or lower end 124 secured to a first follower 126 and a second or upper end 128 operatively interconnected with a rotational mechanism to be described in greater detail below. Intermediate the first and second ends 124, 128, the cable 122 includes an adjustment device such as a turnbuckle 130 to maintain proper tension in the cable and assure that movement at the first end 124 is transferred to the second end 128. In addition, a pulley 132 is preferably disposed adjacent the test chamber 110 and is rotatably supported by a portion of the frame 102. The pulley 132 allows the first end of the cable to be located at a remote position relative to the test chamber, and yet effectively transfers vertical movement of the cable into generally horizontal motion of arm 134 extends between link arms 136. The link arms 136, in turn, are pivotally mounted at their opposite ends to respective support arms 138 that are disposed in generally parallel relation. The support arms 138 are mounted on opposite sides of the test chamber so that reciprocating motion of the second end 128 of the cable is translated into a rocking or limited arcuate motion of the test chamber 110. In this preferred arrangement, the arcuate motion is about a horizontal axis defined by pivotal mounting rod 140. Each end of the rod 140 is received in an elastomeric type material (e.g., rubber) 142 provided at each end of the rod and that is received over ends of parallel plates 144. The plates 144 are rigidly secured to the frame 102. The elastomeric material 142 is compressed when the test chamber is moved through an arc, and thus the elastomeric material 142 and the tension imposed by the turnbuckle 130 together serve as a restoring member configured to urge the first device 120 toward an at rest position.

Figure 4:
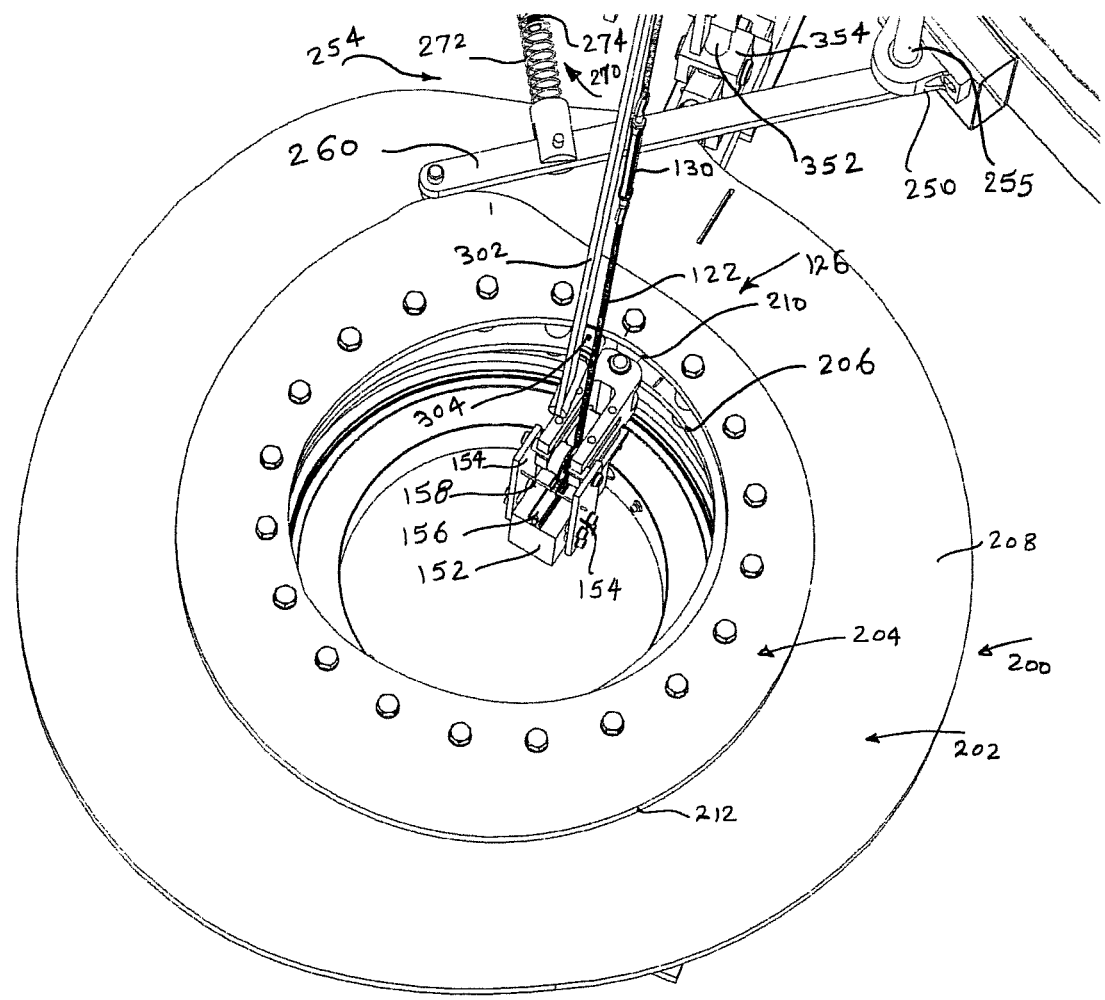
FIG. 4 is an enlarged perspective of inner surface profiles of the first and second cams.
Figure 5:
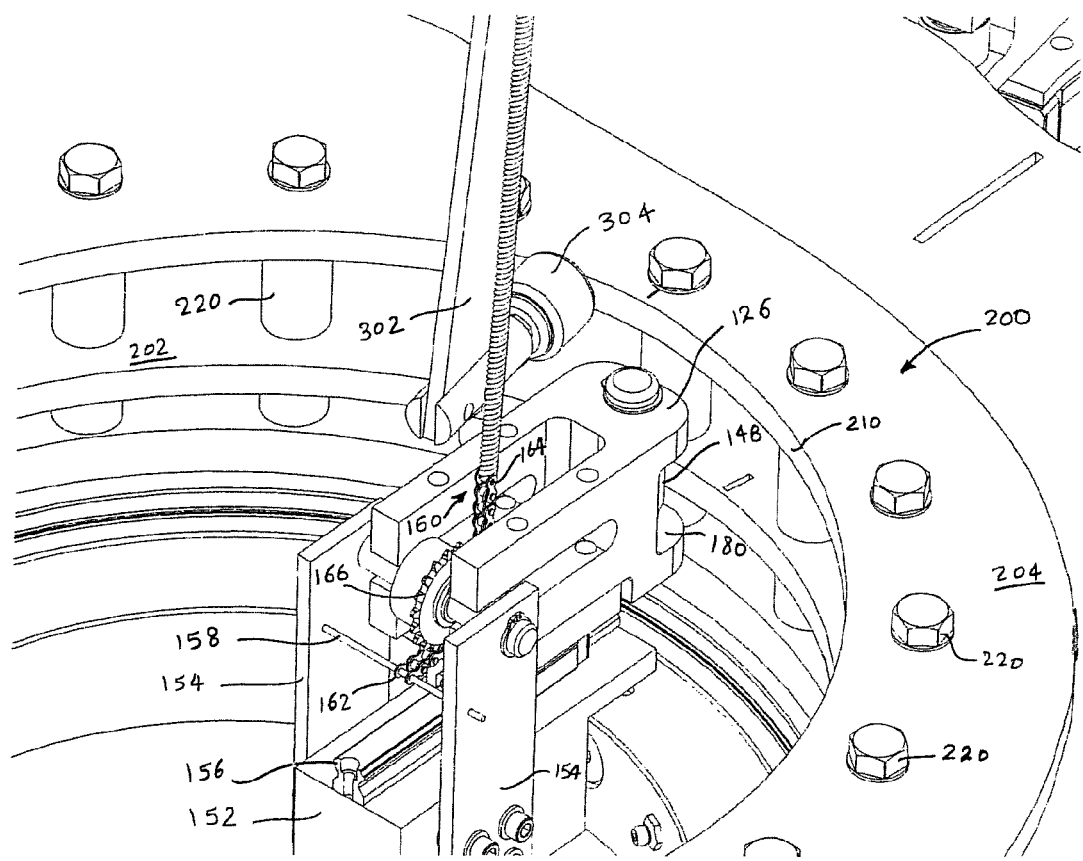
FIG. 5 is a further enlarged perspective of the inner surface profiles of the first and second cams.

The first end 124 of the cable is secured to the first follower 126 (FIGS. 4-5). More specifically, the first follower 126 is an assembly that includes a mount 152 secured to a portion of the frame 102 and having first and second members or mounting plates 154 extending upwardly from opposite sides of the mount. A track or keyway 156 is secured, for example, to an upper surface of the mount 152 at a location between the mounting plates and the track extends in a substantially radial direction. Extending between the mounting plates 154 at a location spaced above the track is a cross member or rod 158. A flexible member such as chain 160 is secured at a first end 162 to the rod 158. The chain 160 continues to a second end 164 that is secured or fixed to the lower end 124 of the cable 122. The chain 160 is partially wrapped about a toothed gear 166 that is rotatably supported for rotation about a horizontal axis by the mounting plates 154. The first follower 126 further includes a slide 180 that moves along the track 156 and includes a channel or groove 182 that together with the track 156 limits movement of a follower surface 184 so that the first follower travels in a generally radial direction and against at least a portion of a drive mechanism or rotary driver 200.

More particularly, the drive mechanism 200 (FIGS. 2-7) includes a first cam 202 and a second cam 204 that are driven by a drive motor M (schematically represented in FIG. 2) for rotation about a vertical axis relative to the frame 102. As illustrated in the drawings, each of the first and second cams 202, 204 is generally annularly shaped and are operatively engaged by followers. More particularly, the first annular cam 202 has a first or inner profile 206 and a second or outer profile 208 (FIG. 4). Likewise, the second cam 204 has a first or inner profile 210 and a second or outer profile 212. The cams 202, 204 are secured together for rotation about a common central or vertical axis. Fasteners such as bolts 220 extend between the annularly shaped cam plates 202, 204 to secure the cam plates together and assure that the cam plates rotate in unison. It is also evident that in this preferred arrangement, the first cam 202 has a larger, outer profile surface 208 than the outer profile 212 of the second cam. On the other hand, the inner profiles 206, 210, of the first and second cams, respectively, have approximately the same inner dimension. It will be appreciated though that the profiles, i.e., the arc or segmented portions that define the circumferentially continuous, inner annular surface or outer annular surface of each cam, may be different depending on the required movements of the followers that track along the surfaces of the profiles in order to translate to desired forces or motions imposed on the test chamber 110.

Thus, the first device 120 imposes a first, rotational motion ($\Theta_y$) on the test chamber 110 or associated specimen 112 as the first cam 202 rotates. The first follower assembly 126, and more particularly surface 184, rides along the first profile 206 of the first cam 202. As the cam profile 206 increases or decreases in radial dimension, the guide 180 which is urged against the cam profile likewise moves radially inward and outward along track 156 thereby resulting in rotation of toothed gear 166 so that the cable 120 moves upwardly and downwardly between the first end 124 and the pulley 132, and the cable moves generally radially between the pulley 132 and the test chamber 110. The ordinarily skilled artisan will appreciate that the mechanical details of a first device that also achieves the same function may differ from that shown and described in the illustrated embodiment; however, the mechanical nature of the first mechanism is advantageously robust, reliable, accurate, inexpensive, etc. and easily synchronized with the other motion producing devices as will become apparent below.

A second device 250 (FIGS. 2-4, 6-8 and 11) is operatively connected to the test chamber 110 and imposes a second, rotational motion on the test chamber or associated specimen. More particularly, this rotational movement is generally defined herein as a rotation about a second axis that results in motion ($\Theta_z$) of the test chamber 110. Here, the second device 250 preferably cooperates with the outer profile 212 of the second cam 204. One skilled in the art will appreciate, however, that the particular selected profile of the first or second cam is not critical, as long as the profile has a shape or conformation that meets the desired parameters of the test protocol. The second device 250 includes an elongated, vertical rod 252 that is operatively connected to a second follower 254 at a first or lower end and includes a drive member or toothed gear 256 at a second or upper end. The second follower 254 includes an arm 260 fixed to the first end of the elongated rod 252 at one end. A roller 262 is provided at a second end of the arm 260 that engages or rides along outer profile 212 of the second cam 204.

A restoring member 270 urges the roller 262 of the second follower 254 against the profile 212. In the illustrated embodiment, the restoring member 270 includes a spring 272 received around a guide member 274 extending outwardly from the frame 102. The other end of the spring 272 is operatively connected to the follower arm 260. As the roller 262 moves radially inward and outward in response to rotation of the cam assembly, the follower arm 260 pivots through a limited arc about the vertical axis defined by the elongated rod 252 of the second drive. Likewise, gear 256 at the upper end of the rod 252 drives a driven gear 280 that is operatively connected to the test chamber 110. The driving engagement between the drive gear 256 and a driven gear 280 is provided via a belt or similar flexible member (represented by dashed line in FIG. 11 but not shown in solid line for ease of illustration). Again, one skilled in the art will appreciate that the mechanical details of a second mechanism that also achieves the same function may differ from that shown and described in the illustrated embodiment; however, the mechanical nature of the second mechanism is advantageously robust, reliable, accurate, inexpensive, etc. and easily synchronized with the other motion producing devices.

Figure 3:
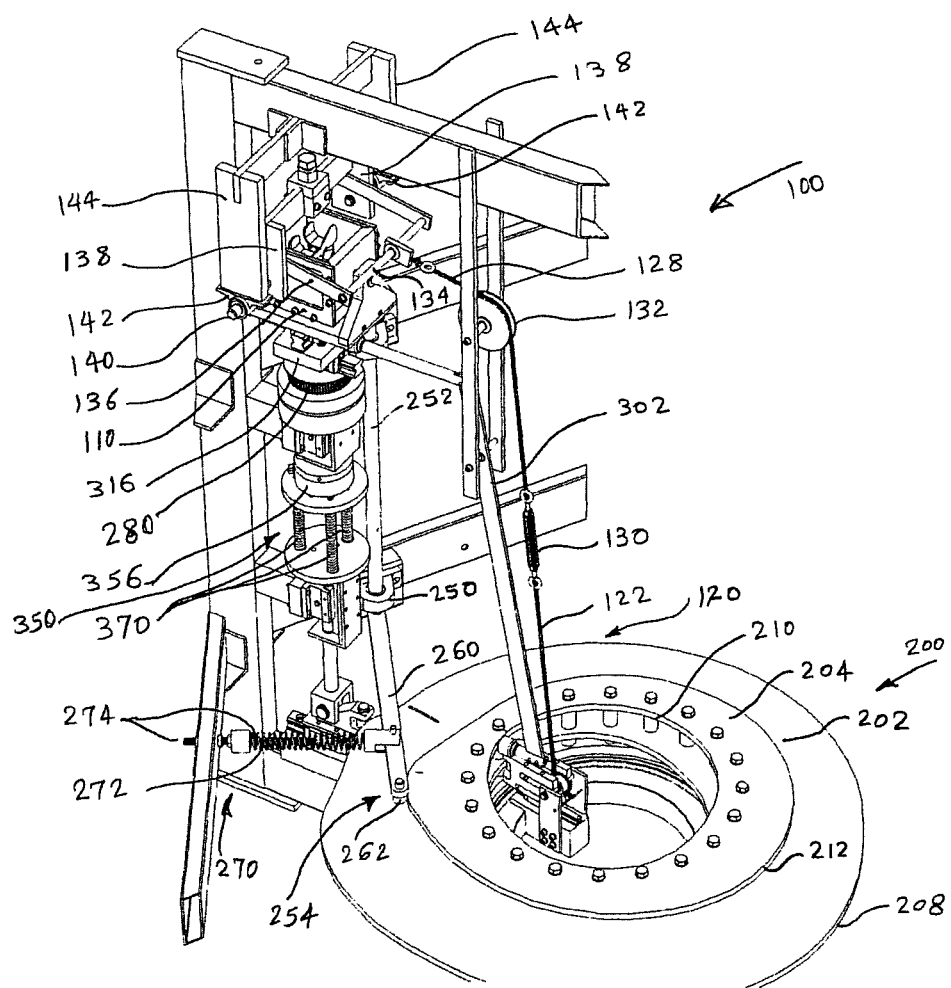
FIG. 3 is a perspective view of a testing apparatus of FIG. 2.
Figure 6:
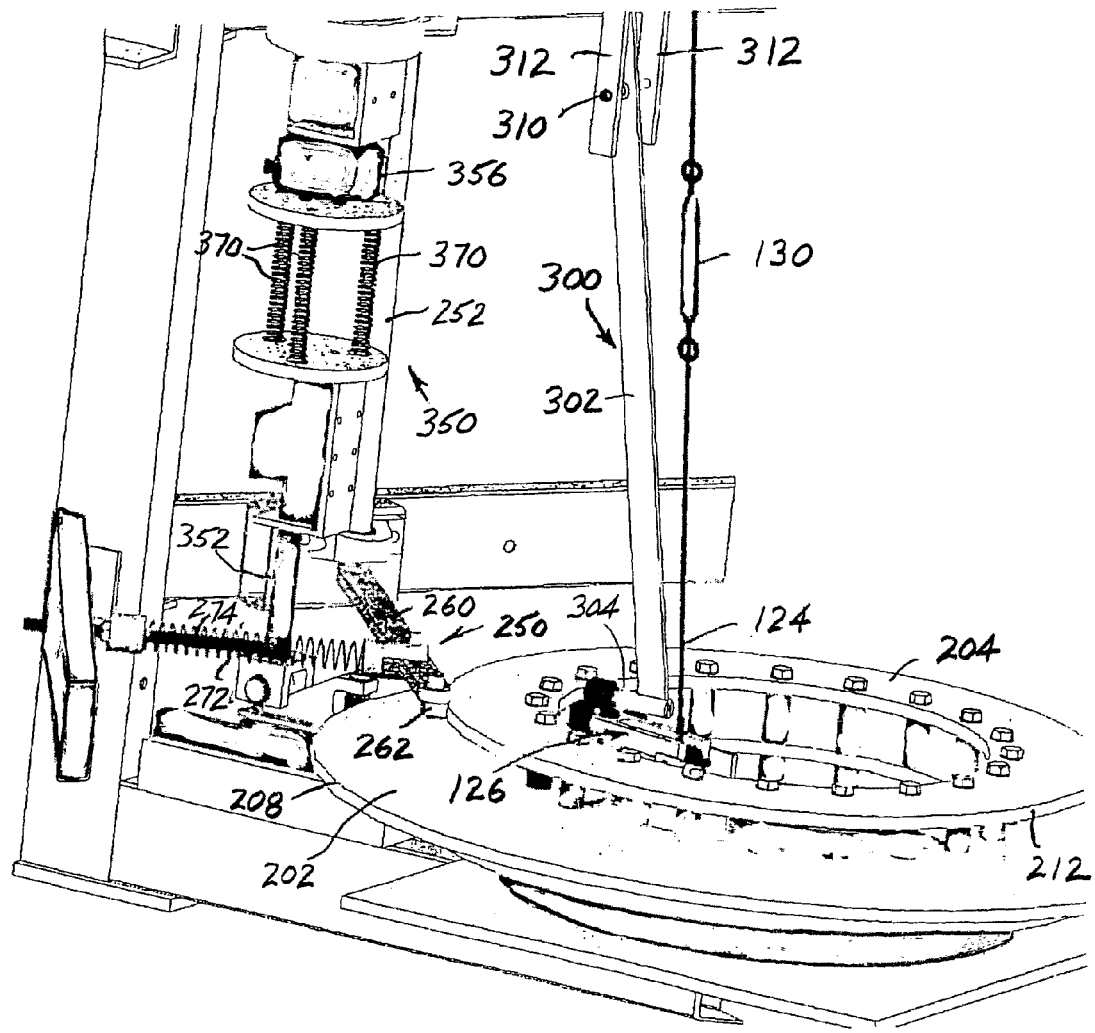
FIG. 6 is an enlarged perspective of the outer surface profiles of the first and second cams.
Figure 7:
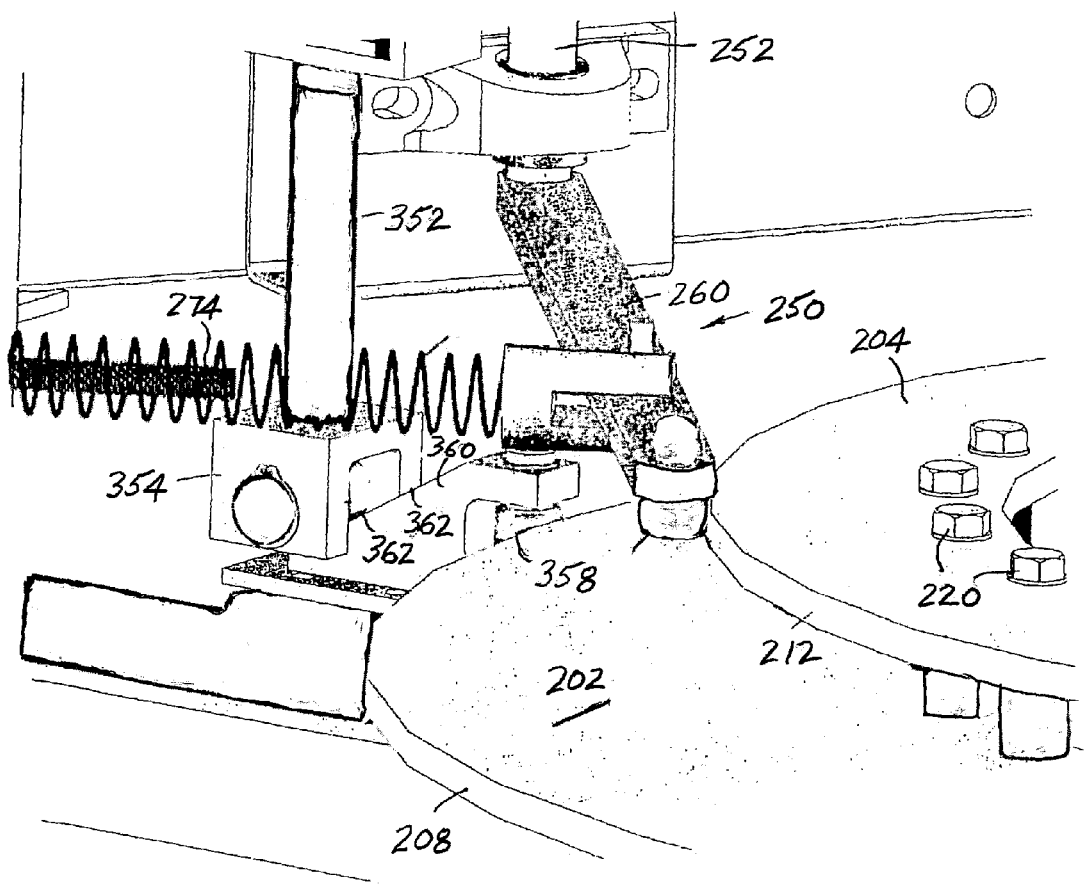
FIG. 7 is a further enlarged perspective view of the outer surface profiles of the first and second cams.
Figure 8:
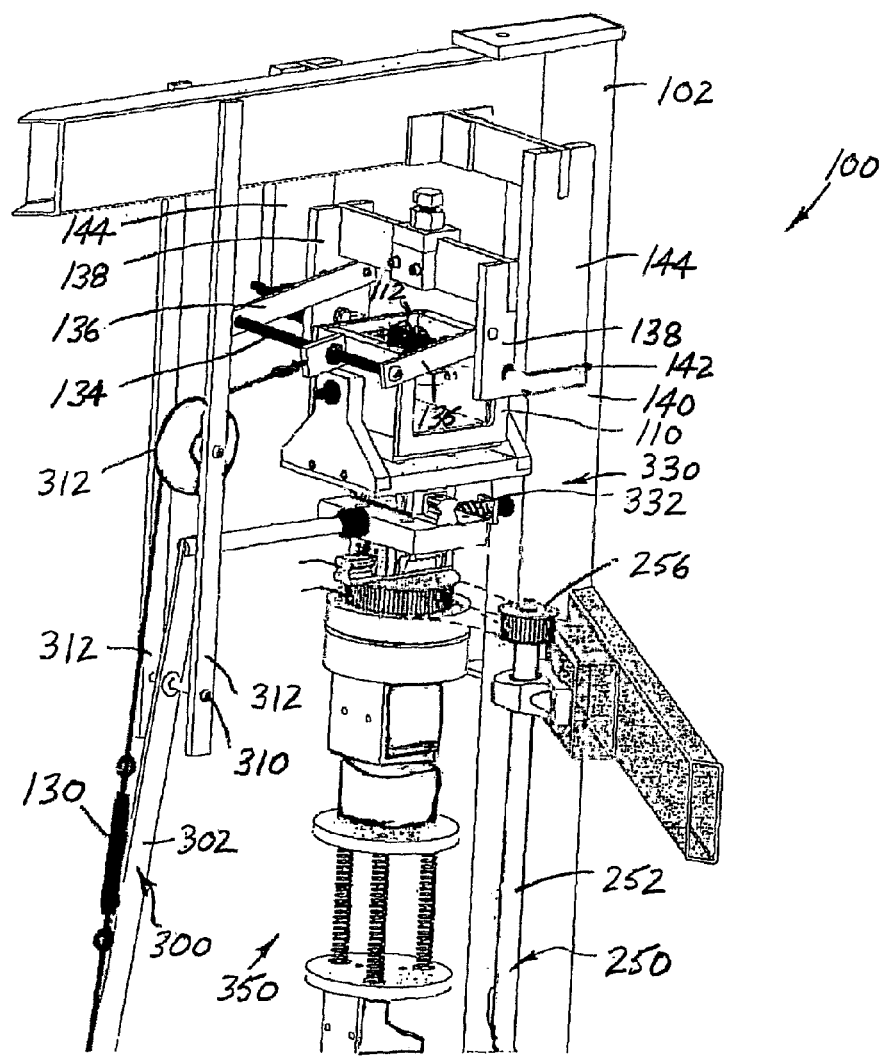
FIG. 8 is a perspective view of test chamber and the four forces/motions imposed thereon.
Figure 9:
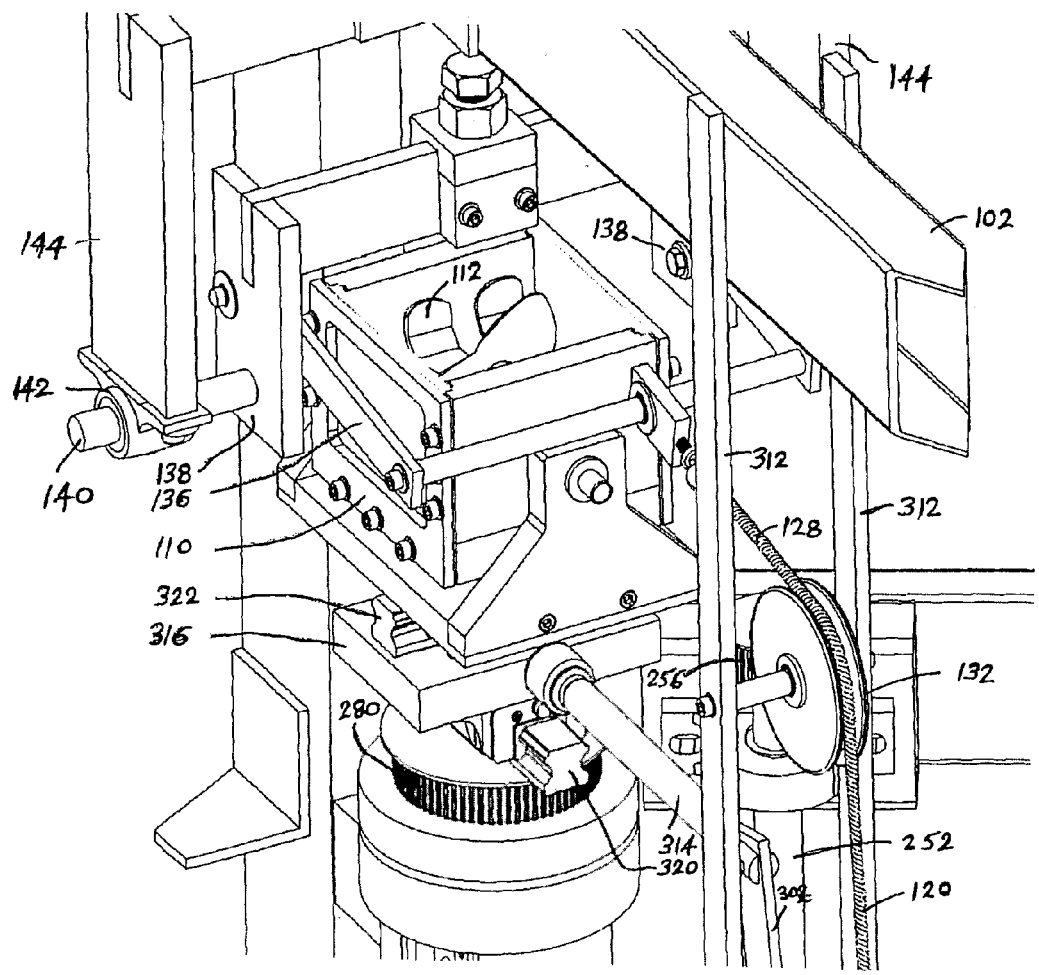
FIG. 9 is an enlarged perspective view of the test chamber.
Figure 10:
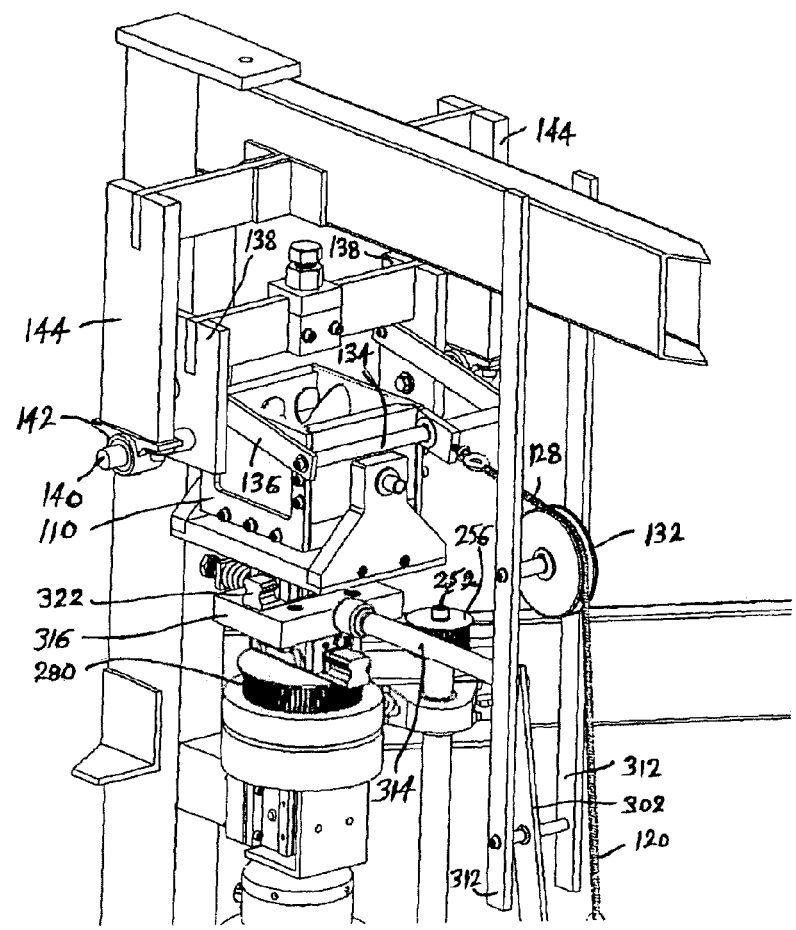
FIG. 10 is another enlarged perspective view of the test chamber.
Figure 11:
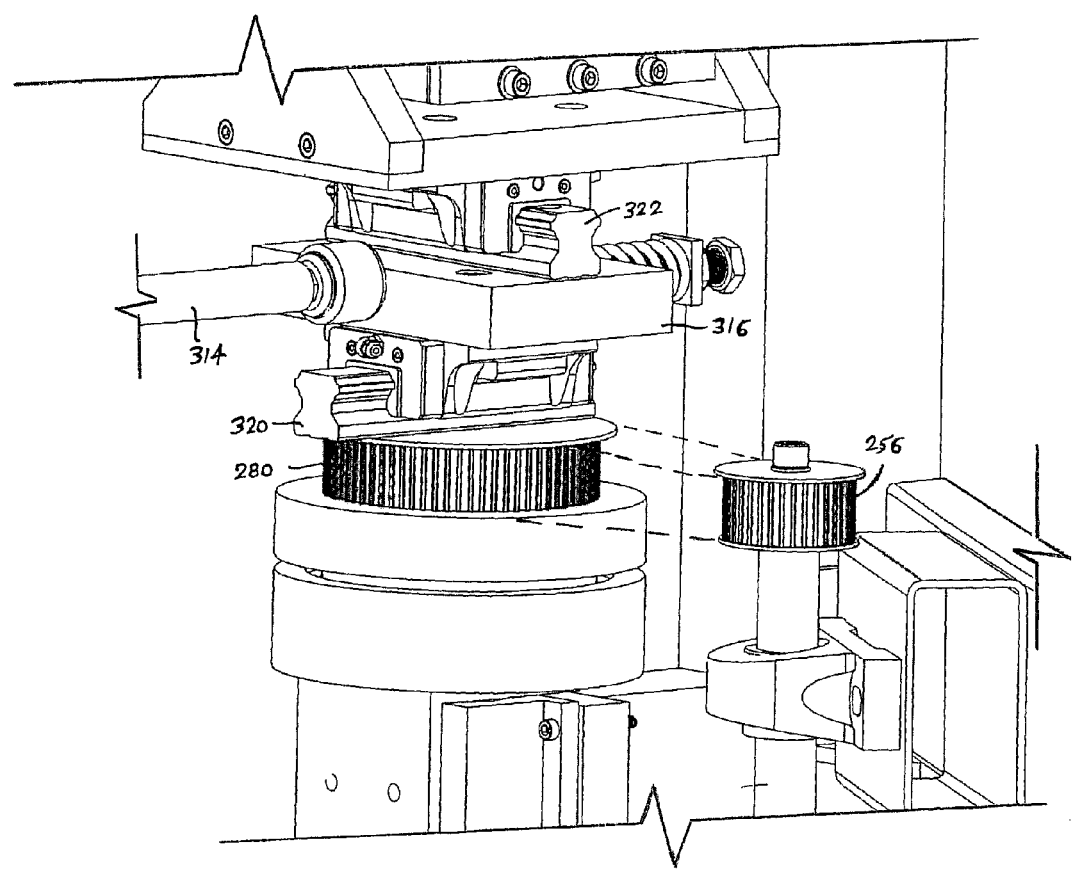
FIG. 11 is an enlarged perspective view of the rotational drive mechanism.

A third device 300 (FIGS. 2-4, 6, and 8-10) is provided for imposing a generally planar movement on the test chamber and associated specimen. This generally planar movement is also referred to as linear translation (X). The third device 300 includes an elongated arm 302 that is secured at a first or lower end to a follower 304 that cooperates with the inner profile 210 of the second cam 204 (FIGS. 3 and 6). A second or upper end of the elongated arm 302 is mounted on a pivot rod 310 that is horizontally arranged between support arms 312 extending downwardly from the frame 102. These support arms 312 in the preferred arrangement are the same arms that support the pulley 132 associated with the first device, although it will be appreciated that this need not necessarily be the case. The elongated arm 302 extends past the pivot rod 310 and is pivotally joined to one end of push member 314. An opposite end of the push member 314 engages planar block 316. Movement of the block 316 is constrained by a key and keyway arrangement 320 (FIGS. 8-10) in one direction. The key/keyway arrangement 320 provides for movement only in the X direction. This assembly 320 is also interposed between the driven gear 280 of the second drive and the test chamber 110.

The restoring member 330 (FIGS. 6 and 8) associated with the third device includes a spring 332 that extends between the frame 102 and the planar block 316. Thus the planar block 316 and push member 314 are urged away from the frame when the follower 304 moves radially outward. The mechanical details of a third mechanism that also achieves the same function may differ from that shown and described in the illustrated embodiment; however, the mechanical nature of the third mechanism is advantageously robust, reliable, accurate, inexpensive, etc. and easily synchronized with the other motion producing devices.

A fourth device or mechanism 350 is operatively connected to the test chamber 110 to impose a dynamic, compressive load force on the associated specimen ($F_z$). More particularly, the fourth device 350 (FIGS. 2 3, 6, and 7) includes a force transmitting rod 352 secured to a follower 354 at a first or lower end, and to a load cell 356 at a second or upper end. The follower 354 includes a roller 358 (FIG. 7) that is urged against the outer profile 208 of the first cam 202. The follower 354 further includes an inclined plane 360 having an angled surface 362 that is operatively engaged by a roller 364. As the inclined plane 360 moves inwardly and outwardly in a generally radial direction, the angled face 362 moves the force transmitting rod 352 upwardly and downwardly in the vertical direction. The vertical force imposed by rod 352 as a result of the inclined plane arrangement is monitored by the load cell 356. In addition, one or more springs 370 are collectively used as the restoring member for urging the fourth follower 354 against the outer profile 208 of the first cam 202. In this manner, the profile 208 of the outer cam profile of the first cam is transmitted into vertical motion or a load ($F_z$) on the test specimen 112.

A preload can also be applied to the test specimen through the fourth device. For example, the force of one or more springs 370 are effective at providing a preload transmitted through the load cell to the test chamber. In addition, the mechanical details of a fourth mechanism that also achieves the same function may differ from that shown and described in the illustrated embodiment; however, the mechanical nature of the fourth mechanism is advantageously robust, reliable, accurate, inexpensive, etc. and easily synchronized with the other motion producing devices. For example, a scissors-type mechanism may be employed that produces substantial vertical motion or force in response to radial movement dictated by the outer profile 208 of the second cam 202. Similarly, a rack and gear assembly can effectively translate radial movement of the cam outer profile 208 into vertical motion that applies a compressive force on the test specimen.

As will be appreciated, the drive mechanism 200 defined in part by cams 202, 204 is driven by a motor (not shown). The cams are rotated about a common axis and in unison. By forming the cams 202, 204 as generally annular members, radially inner and outer surfaces of each of the cams can be used as cam profiles 206, 208 and 210, 212 that operatively engage followers associated with the separate mechanical devices. Specifically, as a result, the first device creates a rotation about one of the axes, the second device imposes a rotation about one of the axes orthogonal to the first, the third device provides linear translation on the specimen along one of the axes, and a fourth device imposes a dynamic, compressive force on the specimen. Each of the first, second, third, and fourth devices includes a corresponding restoring member that is configured in a unique manner to the first, second, third, and fourth followers, respectively, to urge the followers against one of the profile surfaces of the first and second cams.

Figure 12:
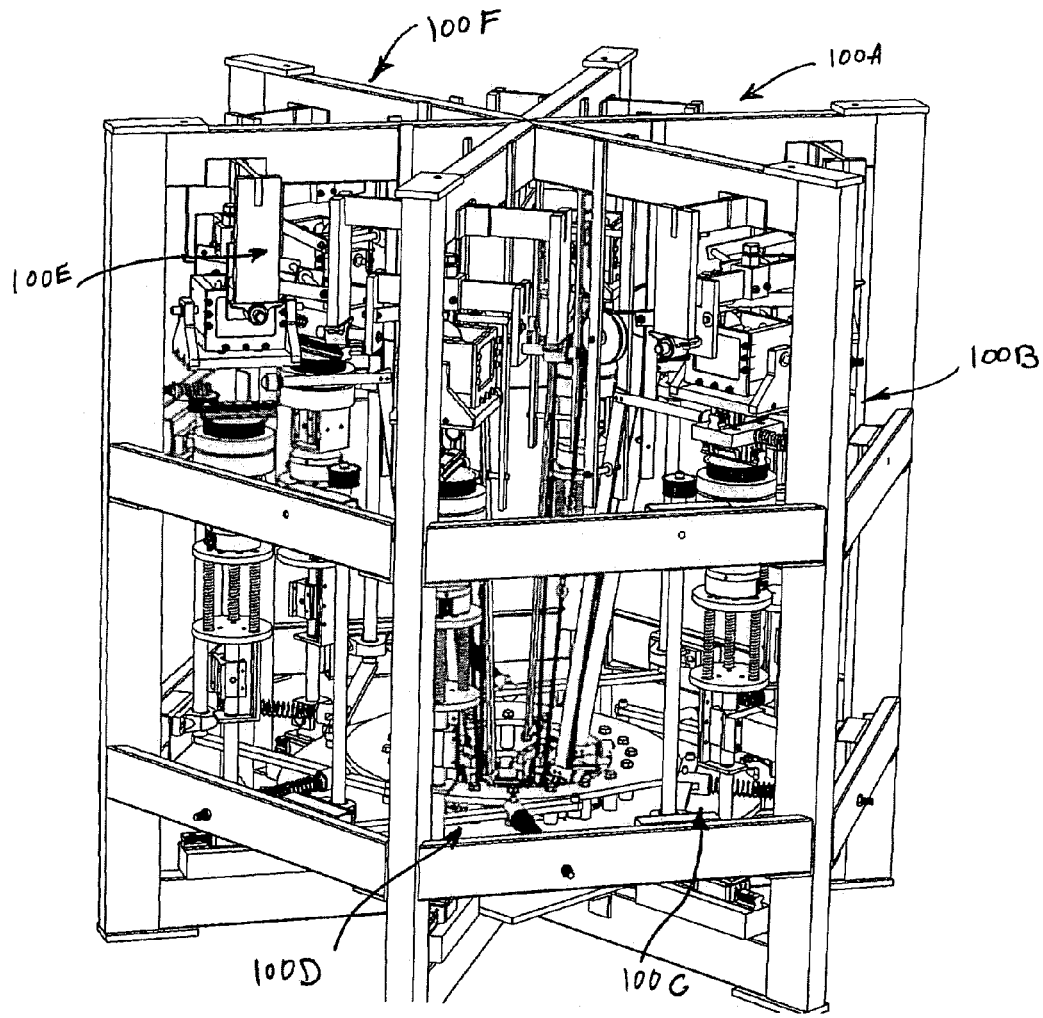
FIG. 12 is a perspective view of a system incorporating individual testing apparatus.
Figure 13:
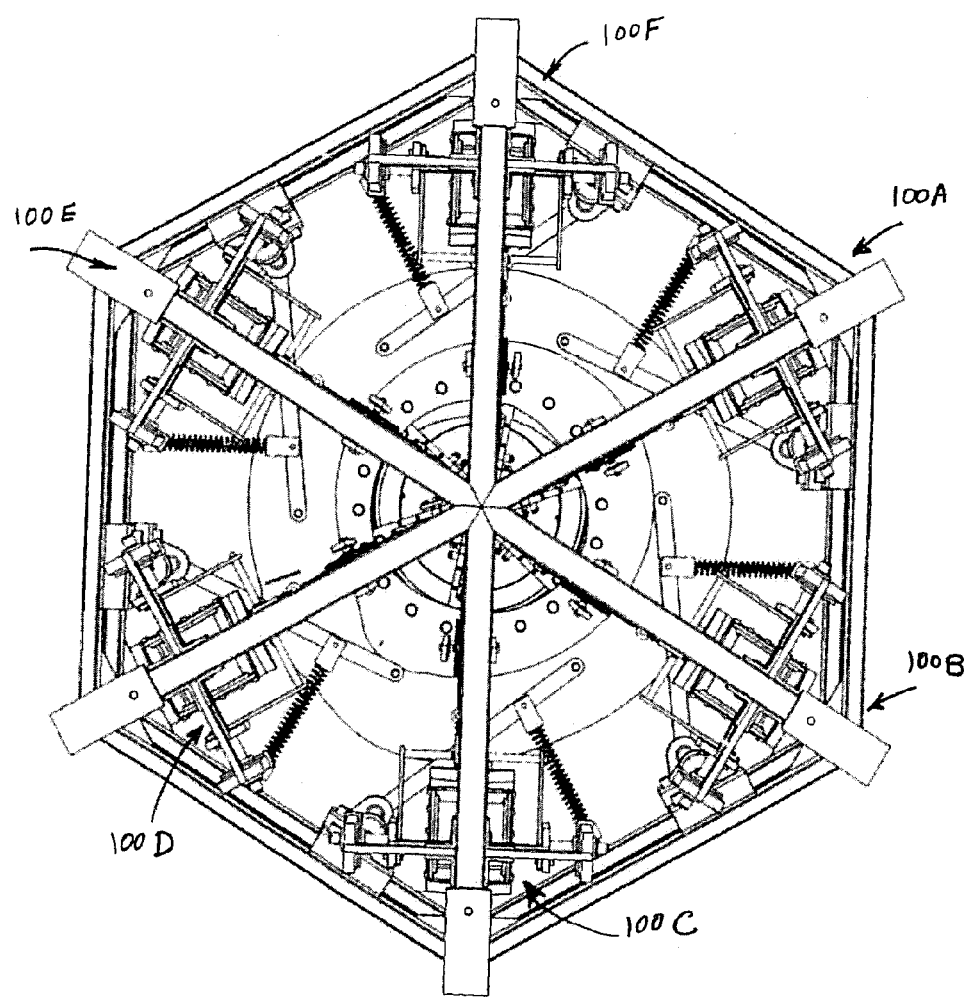
FIG. 13 is a top plan view of the system of FIG. 12.

FIGS. 12 and 13 illustrate that one of these testing apparatus can be replicated or duplicated and assembled into a system that includes a cooperating group of testing apparatus. Shown here are six separate testing apparatus labeled 100A through 100 F. Each mechanism is mounted to be 60° out of phase with the next adjacent testing apparatus. Advantageously, each testing apparatus operates off the same drive mechanism, namely the first and second cams 202, 204. The structure and operation of each testing apparatus is identical to the other so that one test assembly can simultaneously test six separate specimens. The design of the profile surfaces of the respective cams assures that each testing apparatus is simultaneously undergoing the same four actions ($M_y$, $M_z$, $F_x$, and $F_z$) provided by the first, second, third, and fourth devices as described above. In other words, each of the four devices associated with one testing apparatus are coordinated or synchronized with one another, and in addition all of the four devices in each of the six testing apparatus are likewise coordinated or synchronized with the four devices of the other testing apparatus in the test system.

This written description uses examples to describe the disclosure, including the best mode, and also to enable any person skilled in the art to make and use the disclosure. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A testing apparatus for exposing an associated specimen to movement along multiple axes, the testing apparatus comprising:
    a test chamber dimensioned to receive the associated specimen;
    a first device operatively connected to the test chamber to impose a first, rotational movement on the associated specimen;
    a second device operatively connected to the test chamber to impose a second, rotational movement different than the first movement on the associated specimen;
    a third device operatively connected to the test chamber to impose only a linear translation on the associated specimen;
    a fourth device operatively connected to the test chamber to impose a dynamic force on the associated specimen; and
    a drive mechanism operatively connected to the first, second, third, and fourth devices so that the movements and force imposed by respective ones of the devices are commonly driven by the drive mechanism.

2. The testing apparatus of claim 1 wherein the first device is configured to rotate the associated specimen about one of the axes of an orthogonal coordinate system fixed in space.

3. The testing apparatus of claim 2 wherein the second device is configured to rotate the associated specimen about a second axis of the said coordinate system.

4. The testing apparatus of claim 3 wherein the third device is configured to apply a linear translation along the third axis of the said coordinate system to the associated specimen.

5. The testing apparatus of claim 4 wherein the fourth device is configured to impose a periodic force on the associated specimen.

6. The testing apparatus of claim 1 wherein each of the first, second, third, and fourth devices is configured to operatively engage the drive mechanism so that the movements and force imposed by respective ones of the devices are commonly driven with one another.

7. The testing apparatus of claim 6 wherein the drive mechanism includes first and second cams that rotate about a common axis.

8. The testing apparatus of claim 7 further comprising first, second, third, and fourth followers associated with the first, second, third and fourth devices, respectively, where each follower operatively engages one of the first and second cams.

9. The testing apparatus of claim 7 wherein each of the first, second, third, and fourth devices includes a restoring member configured to urge the first, second, third, and fourth followers against one of the first and second cams.

10. The testing apparatus of claim 7 wherein each of the cams is generally annularly shaped, and wherein the first follower associated with the first device operatively engages one of inner and outer profiled surfaces of the first cam, a second follower associated with the second device operatively engages the other of the inner and outer profiled surfaces of the first cam, a third follower associated with the third device operatively engages one of inner and outer profiled surfaces of the second cam, and a fourth follower associated with the fourth device operatively engages the other of the inner and outer profiled surfaces of the second cam.

11. The testing apparatus of claim 1 further comprising
a drive mechanism operatively connected to the first, second, third, and fourth devices so that the movements and force imposed by respective ones of the devices are fixed relative to with one another; and
additional testing apparatus identical to the testing apparatus and each operatively driven by the drive mechanism.

12. The testing apparatus of claim 11 wherein the additional testing apparatus includes second, third, fourth, fifth, and sixth testing apparatus wherein each of the first, second, third and fourth devices in each are fixed relative to one another by first and second cams that are commonly driven together.

13. A method of testing a specimen comprising:
placing a specimen in a test chamber;
imposing a force on the specimen;
providing linear translation only along a first axis of a fixed orthogonal coordinate system on the specimen;
applying two rotations to the specimen along remaining, second and third orthogonal axes of the fixed coordinate system; and
commonly driving a dynamic load, linear translation, and the two rotations with a drive mechanism.

14. The method of claim 13 wherein the force imposing step includes applying a periodic, force on the specimen.

15. The method of claim 13 wherein the commonly driving step includes rotating first and second cams together.

16. The method of claim 15 further comprising providing first, second, third, and fourth followers that operatively engage at least one of the first and second cams for providing mechanical force imposition, linear translation and two rotations to the specimen.

17. The method of claim 16 wherein the driving step includes providing first and second generally annular cams rotated about a single axis, each of the first and second cams has an inner and an outer profile, and the first follower operatively engages the inner profile of the first cam, the second follower operatively engages the outer profile of the first cam, the third follower operatively engages the inner profile of the second cam, and the fourth follower operatively engages the outer profile of the second cam.

18. The method of claim 17 wherein the method further includes urging each of the first, second, third, and fourth followers against a respective profile.

19. The method of claim 13 further includes assembling multiple testing apparatus together in a coordinated configuration in order to test multiple, individual specimens under the same conditions.

20. The method of claim 19 wherein the assembly of multiple testing apparatus is commonly driven by first and second cams.

* * * * *